US010023516B2

(12) United States Patent
Brammer et al.

(10) Patent No.: US 10,023,516 B2
(45) Date of Patent: Jul. 17, 2018

(54) HYDROFORMYLATION PROCESS

(71) Applicant: Dow Technology Investments LLC, Midland, MI (US)

(72) Inventors: Michael A. Brammer, Freeport, TX (US); George R. Phillips, South Charleston, WV (US); Thomas C. Eisenschmid, South Charleston, WV (US); Irvin B. Cox, The Villages, FL (US); Robert Hetterley, Stockton-on-Tees (GB); Michael John Bainbridge, North Yorkshire (GB)

(73) Assignee: Dow Technology Investments LLC, Midland, MI (US)

( * ) Notice: Subject to any disclaimer, the term of this patent is extended or adjusted under 35 U.S.C. 154(b) by 0 days.

(21) Appl. No.: 15/522,137

(22) PCT Filed: Nov. 18, 2015

(86) PCT No.: PCT/US2015/061332
§ 371 (c)(1),
(2) Date: Apr. 26, 2017

(87) PCT Pub. No.: WO2016/089602
PCT Pub. Date: Jun. 9, 2016

(65) Prior Publication Data
US 2017/0355656 A1 Dec. 14, 2017

Related U.S. Application Data

(60) Provisional application No. 62/087,572, filed on Dec. 4, 2014.

(51) Int. Cl.
*C07C 45/50* (2006.01)
*B01J 31/00* (2006.01)
*B01J 31/18* (2006.01)

(52) U.S. Cl.
CPC ............ *C07C 45/50* (2013.01); *B01J 31/185* (2013.01); *B01J 2231/321* (2013.01); *B01J 2531/822* (2013.01)

(58) Field of Classification Search
CPC .............................. C07C 45/50; B01J 31/125
USPC .................................................. 568/450, 454
See application file for complete search history.

(56) References Cited

U.S. PATENT DOCUMENTS

| | | |
|---|---|---|
| 3,415,906 A | 12/1968 | Shepard et al. |
| 3,527,809 A | 9/1970 | Pruett et al. |
| 4,148,830 A | 4/1979 | Pruett et al. |
| 4,247,486 A | 1/1981 | Brewester et al. |
| 4,329,507 A | 5/1982 | Takeda et al. |
| 4,518,809 A | 5/1985 | Forster et al. |
| 4,528,403 A | 7/1985 | Tano et al. |
| 4,567,302 A | 1/1986 | Sivaramakrishnan |
| 4,567,306 A | 1/1986 | Dennis et al. |
| 4,599,206 A | 7/1986 | Billig et al. |
| 4,668,651 A | 5/1987 | Billig et al. |
| 4,717,775 A | 1/1988 | Billig et al. |
| 4,737,588 A | 4/1988 | Billig et al. |
| 4,748,261 A | 5/1988 | Billig et al. |
| 4,769,498 A | 9/1988 | Billig et al. |
| 4,774,361 A | 9/1988 | Maher et al. |
| 4,835,299 A | 5/1989 | Maher et al. |
| 4,885,401 A | 12/1989 | Billig et al. |
| 5,001,274 A | 3/1991 | Bunning |
| 5,102,505 A | 4/1992 | Sorensen |
| 5,110,990 A | 5/1992 | Blessing et al. |
| 5,113,022 A | 5/1992 | Abatjoglou et al. |
| 5,179,055 A | 1/1993 | Wink et al. |
| 5,202,297 A | 4/1993 | Lorz et al. |
| 5,235,113 A | 8/1993 | Sato et al. |
| 5,254,741 A | 10/1993 | Lorz et al. |
| 5,264,616 A | 11/1993 | Roeper et al. |
| 5,277,532 A | 1/1994 | Pazzaglia |
| 5,312,996 A | 5/1994 | Packett |
| 5,360,938 A | 11/1994 | Babin et al. |
| 5,364,950 A | 11/1994 | Babin et al. |
| 5,391,801 A | 2/1995 | Sato et al. |
| 5,426,238 A | 6/1995 | Mod et al. |
| 5,426,239 A | 6/1995 | Dressaire et al. |
| 5,491,266 A | 2/1996 | Babin et al. |
| 5,527,950 A | 6/1996 | Hansen et al. |
| 5,648,553 A | 7/1997 | Ueda et al. |
| 5,731,472 A | 3/1998 | Leung et al. |
| 5,741,944 A | 4/1998 | Bryant et al. |
| 5,929,289 A | 7/1999 | Abatjoglou et al. |
| 6,100,432 A | 8/2000 | Borgel et al. |
| 6,172,267 B1 | 1/2001 | Urata et al. |
| 6,500,991 B2 | 12/2002 | Wiese et al. |
| 6,841,502 B2 | 1/2005 | Boussie et al. |
| 6,852,661 B1 | 2/2005 | Ahlers et al. |
| 7,446,231 B2 | 11/2008 | Peterson et al. |
| 7,863,487 B2 | 1/2011 | Eisenschmid et al. |
| 8,404,903 B2 | 3/2013 | Cox et al. |
| 8,609,794 B2 | 12/2013 | Klosin et al. |
| 9,422,383 B2 | 8/2016 | LiPiShan et al. |
| 9,428,433 B2 | 8/2016 | Fridag et al. |
| 2002/0065437 A1 | 5/2002 | Wiese et al. |
| 2011/0269997 A1* | 11/2011 | Cox ........................ C07C 45/50 568/456 |
| 2011/0282018 A1 | 11/2011 | Klosin et al. |

FOREIGN PATENT DOCUMENTS

| | | |
|---|---|---|
| CN | 102826972 A | 12/2012 |
| KR | 1060375 | 8/2011 |
| KR | 2011116629 | 10/2011 |

OTHER PUBLICATIONS

Bringham Et. Al. Atropo-enantioselective synthesis of a C3-symmetric tripodal ligand with three axially chiral biratyl subunits, Tetrabhedron: Asymmetry 14(2003) 2225-2228.
(Continued)

*Primary Examiner* — Sikarl A Witherspoon

(57) ABSTRACT

Catalytic metal loss when using a hydroformylation catalyst comprising an organophosphite ligand is ameliorated by adding CO to a strip gas vaporizer.

12 Claims, 1 Drawing Sheet

(56) References Cited

OTHER PUBLICATIONS

PCT/US2015/061332, International Search Report and Written Opinion dated Feb. 5, 2016.
PCT/US2015/061332, International Preliminary Report on Patentability dated Feb. 5, 2017.
PCT/US2015/061332, Response Written Opinion dated Oct. 3, 2016.
PCT/US2015/061332, Written Opinion dated Nov. 23, 2016.
Van Leeuwen, Peit. Eds. "Rhodium Catalyzed Hydroformylation," van Leeuwen, Claver, Kluwer Academic Pub. Chapters 3, 8 and 9 2000.

* cited by examiner

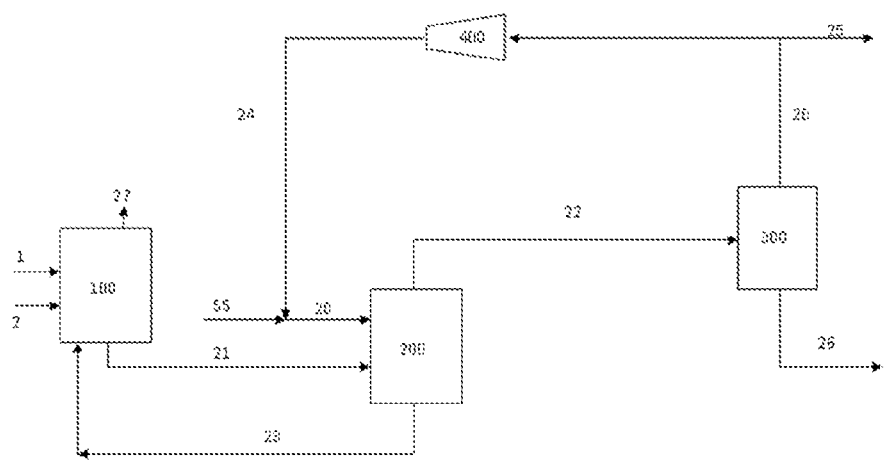

HYDROFORMYLATION PROCESS

BACKGROUND OF THE INVENTION

The invention relates to a hydroformylation process. More specifically it relates to such a process wherein the amount of heavies in a catalyst recycle stream is controlled.

It is well known that aldehydes can be produced by reacting olefins with carbon monoxide and hydrogen in the presence of a metal-organophosphorus ligand complex catalyst, and that preferred processes involve continuous hydroformylation and recycling of a catalyst solution containing a metal-organophosphorus ligand complex catalyst wherein the metal is selected from Groups 8, 9, or 10. Rhodium is a preferred Group 9 metal. U.S. Pat. No. 4,148,830, U.S. Pat. No. 4,717,775, and U.S. Pat. No. 4,769,498 disclose examples of this process. The resulting aldehydes can be used to produce a host of products including alcohols, amines, and acids. It is common practice to employ a vaporizer following the reaction zone for the purpose of separating products from the catalyst.

It is known that hydroformylation catalysts comprising rhodium and organophosphite ligands are capable of very high reaction rates; see, "Rhodium Catalyzed Hydroformylation," van Leeuwen, Claver, Kluwer Academic Pub. (2000). Such catalysts have industrial utility, as they can be used to increase production rates, or to efficiently hydroformylate internal and/or branched internal olefins, which react more slowly than linear alpha olefins. However, it is also known, e.g., from U.S. Pat. No. 4,774,361, that under some conditions these catalysts lose rhodium in liquid recycle hydroformylation processes. A continuous loss of rhodium can increase catalyst costs dramatically, as rhodium is prohibitively expensive.

Although the exact cause of rhodium loss is unclear, it has been hypothesized in U.S. Pat. No. 4,774,361 and elsewhere that the loss is exacerbated by the low concentration of carbon monoxide (CO) and high temperature environment of a typical product separation step. U.S. Pat. No. 6,500,991 describes a means of slowing the loss of rhodium in an organophosphite-promoted process by cooling the concentrated catalyst following product removal, and then adding CO to the concentrated stream. U.S. Pat. No. 6,500,991 also describes adding CO to a depressurization/flash vessel prior to the separation step. For either option, the total pressure in the separation zone is taught to be less than or equal to 1 bar. Thus, the process of U.S. Pat. No. 6,500,991 attempts to stabilize the catalyst before and after the separation zone without directly addressing losses that may occur during the harsh environment of the separation step.

U.S. Pat. No. 8,404,903 describes a means of removing aldehyde product at greater than atmospheric pressure while employing relatively moderate temperatures. However, that process offers no means to control the CO content beyond changing the condenser temperature of the separation zone. This means of control is limited to a narrow range of CO partial pressures and requires an expensive refrigeration unit to condition such a large flow of gases. At the maximum total pressure (100 psia) and mole percent CO (16%) described in U.S. Pat. No. 8,404,903, a maximum CO partial pressure of 16 psia is possible, although at this high pressure, the separation zone production rate is unacceptably low, even for removal of the relatively volatile $C_5$ aldehyde. This is due to the fact that an acceptable balance of vaporizer temperature and recycle gas flow are required to achieve an acceptable product recovery rate and rate of rhodium loss. U.S. Pat. No. 8,404,903 mentions that the presence of CO in the recycle gas should be beneficial for stability of the phosphite ligand, but there is no mention of slowing or preventing rhodium loss.

In view of the deficiencies of the prior art, there remains a need for a means of separating high boiling aldehydes from a rhodium-organophosphite hydroformylation catalyst while reducing the loss of rhodium.

SUMMARY OF THE INVENTION

The process of the invention is such a continuous hydroformylation process comprising: (a) removing from a reactor a crude product; (b) sending the crude product to a vaporizer; (c) separating the crude product in the vaporizer to produce a catalyst-containing liquid stream and a gas phase stream; and (d) maintaining an average CO partial pressure in the vaporizer of greater than 16 psia (110 kPa).

In one embodiment, the process comprises:
(a) feeding a crude product stream comprising one or more products, one or more heavy by-products, a transition metal-organophosphite ligand complex catalyst, one or more unconverted reactants, and one or more inert lights into a vaporizer;
(b) removing from the vaporizer an overhead gas stream comprising one or more products, one or more unconverted reactants, one or more inert lights, and a portion of the heavy by-products, and feeding said overhead gas stream into a condenser;
(c) removing from the condenser a condenser overhead gas stream comprising one or more unconverted reactants and one or more inert lights;
(d) recycling at least a portion of said condenser overhead gas stream to the vaporizer;
(e) introducing to the vaporizer, in addition to the condenser overhead gas stream, a gas stream comprising CO, such that the average CO partial pressure in the vaporizer is greater than 16 psia (110 kPa); and
(f) removing as a tails stream from the vaporizer, a liquid recycle catalyst stream comprising the transition metal-organophosphite ligand complex catalyst and the balance of the heavy by-products.

Superatmospheric pressure is normally avoided as a process condition for the vaporization of $C_5$ and higher aldehydes. Thus, it is surprising that increasing the CO partial pressure in the harsh, superatmospheric pressure environment of the vaporizer stabilizes a rhodium-organophosphite catalyst, while simultaneously allowing removal of such high boiling aldehydes at moderate temperatures.

BRIEF DESCRIPTION OF THE DRAWINGS

FIG. 1 is a schematic flowsheet of one embodiment of the process of the present invention.

DETAILED DESCRIPTION OF THE INVENTION

A hydroformylation process comprises contacting CO, $H_2$, and at least one olefin under hydroformylation conditions sufficient to form at least one aldehyde product in the presence of a catalyst comprising, as components, a transition metal and a hydrolyzable ligand. Optional process components include an amine and/or water.

All references to the Periodic Table of the Elements and the various groups therein are to the version published in the CRC Handbook of Chemistry and Physics, 72nd Ed. (1991-1992) CRC Press, at page I-11.

Unless stated to the contrary, or implicit from the context, all parts and percentages are based on weight and all test methods are current as of the filing date of this application. For purposes of United States patent practice, the contents of any referenced patent, patent application or publication are incorporated by reference in their entirety (or its equivalent US version is so incorporated by reference) especially with respect to the disclosure of definitions (to the extent not inconsistent with any definitions specifically provided in this disclosure) and general knowledge in the art.

As used herein, "a," "an," "the," "at least one," and "one or more" are used interchangeably. The terms "comprises," "includes," and variations thereof do not have a limiting meaning where these terms appear in the description and claims. Thus, for example, an aqueous composition that includes particles of "a" hydrophobic polymer can be interpreted to mean that the composition includes particles of "one or more" hydrophobic polymers.

Also herein, the recitations of numerical ranges by endpoints include all numbers subsumed in that range (e.g., 1 to 5 includes 1, 1.5, 2, 2.75, 3, 3.80, 4, 5, etc.). For the purposes of the invention, it is to be understood, consistent with what one of ordinary skill in the art would understand, that a numerical range is intended to include and support all possible sub ranges that are included in that range. For example, the range from 1 to 100 is intended to convey from 1.01 to 100, from 1 to 99.99, from 1.01 to 99.99, from 40 to 60, from 1 to 55, etc. Also herein, the recitations of numerical ranges and/or numerical values, including such recitations in the claims, can be read to include the term "about." In such instances the term "about" refers to numerical ranges and/or numerical values that are substantially the same as those recited herein.

As used herein, the terms "ppm" and "ppmw" mean parts per million by weight.

For purposes of this invention, the term "hydrocarbon" is contemplated to include all permissible compounds having at least one hydrogen and one carbon atom. Such permissible compounds may also have one or more heteroatoms. In a broad aspect, the permissible hydrocarbons include acyclic (with or without heteroatoms) and cyclic, branched and unbranched, carbocyclic and heterocyclic, aromatic and nonaromatic organic compounds that can be substituted or unsubstituted.

As used herein, the term "substituted" is contemplated to include all permissible substituents of organic compounds unless otherwise indicated. In a broad aspect, the permissible substituents include acyclic and cyclic, branched and unbranched, carbocyclic and heterocyclic, aromatic and nonaromatic substituents of organic compounds. Illustrative substituents include, for example, alkyl, alkyloxy, aryl, aryloxy, hydroxyalkyl, aminoalkyl, in which the number of carbons can range from 1 to 20 or more, preferably from 1 to 12, as well as hydroxy, halo, and amino. The permissible substituents can be one or more and the same or different for appropriate organic compounds. This invention is not intended to be limited in any manner by the permissible substituents of organic compounds.

The terms "reaction fluid," "reaction medium" and "catalyst solution" are used interchangeably herein, and may include, but are not limited to, a mixture comprising: (a) a metal-organophosphorous ligand complex catalyst, (b) free organophosphorous ligand, (c) aldehyde product formed in the reaction, (d) unreacted reactants, (e) a solvent for said metal-organophosphorous ligand complex catalyst and said free organophosphorous ligand, and, optionally, (f) one or more phosphorus acidic compounds formed in the reaction (which may be homogeneous or heterogeneous, and these compounds include those adhered to process equipment surfaces). The reaction fluid can encompass, but is not limited to, (a) a fluid in a reaction zone, (b) a fluid stream on its way to a separation zone, (c) a fluid in a separation zone, (d) a recycle stream, (e) a fluid withdrawn from a reaction zone or separation zone, (f) a withdrawn fluid being treated with an aqueous buffer solution, (g) a treated fluid returned to a reaction zone or separation zone, (h) a fluid in an external cooler, and (i) ligand decomposition products and their salts.

"Hydrolyzable phosphorous ligands" are trivalent phosphorous ligands that contain at least one P—Z bond wherein Z is oxygen, nitrogen, chlorine, fluorine or bromine. Examples include, but are not limited to, phosphites, phosphino-phosphites, bisphosphites, phosphonites, bisphosphonites, phosphinites, phosphoramidites, phosphino-phosphoramidites, bisphosphoramidites, fluorophosphites, and the like. The ligands may include chelate structures and/or may contain multiple P—Z moieties such as polyphosphites, polyphosphoramidites, etc. and mixed P—Z moieties such as phosphite-phosphoramidites, flurophosphite-phosphites, and the like.

The term "complex" as used herein means a coordination compound formed by the union of one or more electronically rich molecules or atoms (i.e., ligand) with one or more electronically poor molecules or atoms (i.e., transition metal). For example, the organophosphorous ligand employable herein possesses one phosphorus (III) donor atom having one unshared pair of electrons, which is capable of forming a coordinate covalent bond with the metal. A polyorganophosphorous ligand employable herein possesses two or more phosphorus (III) donor atoms, each having one unshared pair of electrons, each of which is capable of forming a coordinate covalent bond independently or possibly in concert (for example, via chelation) with the transition metal. Carbon monoxide can also be present and complexed with the transition metal. The ultimate composition of the complex catalyst may also contain an additional ligand(s) such as described above, for example, hydrogen, mono-olefin, or an anion satisfying the coordination sites or nuclear charge of the metal.

For the purposes of this invention, the terms "heavy by-products" and "heavies" are used interchangeably and refer to hydroformylation process liquid by-products that have a normal boiling point that is at least 25° C. above the normal boiling point of the desired product of the process. In a hydroformylation reaction, for example, where the reactant comprises one or more olefins, the desired product frequently comprises one or more isomeric aldehydes, as well as heavies.

For the purposes of this invention, the terms "feed to tails" and "feed to tails ratio" are used interchangeably and refer to the mass of reaction fluid entering the separation zone relative to the mass of concentrated effluent (vaporizer tails) leaving the bottom of the separation zone and returning to the first hydroformylation reactor. "Feed to tails" is an indicator of the rate at which volatiles, such as aldehyde product, are removed from the reaction fluid. For example, a "feed to tails ratio" of 2, means that the weight of reaction fluid entering the separation zone is two times greater than the weight of the concentrated effluent returned to the first reactor.

For purposes of this invention, the terms "knock-out pot", "knock-out vessel" and "flash vessel" are used interchangeably and refer to low pressure sections between the reaction zone and the vaporizer. The flash vessel allows the reaction fluid to rapidly degas and facilitates control of the vaporizer partial pressures. Such vessels are typically maintained at pressures and temperatures well below those established in the hydroformylation reactors.

For the purposes of this invention, the term "lights" refers to materials that have a normal boiling point of 25° C. or less at atmospheric pressure. As used herein, the term "inert lights" or "light inerts" refers to lights that are essentially unreactive in the process. "Reactive lights" shall refer to lights that are reactive to a significant degree in the process. As an example, in a hydroformylation process, reactive lights include carbon monoxide and hydrogen; while inert lights include alkanes, such as alkanes that are present in the olefinic feed to the reaction, and other inert gases such as nitrogen.

"Essentially isobarically" and like terms mean at essentially constant pressure or within a pressure difference of 1 bar (100 kPa) or less, preferably 0.5 bar (50 kPa) or less. In other words, in one embodiment of the invention the maximum pressure difference across the product phase stripper and the product condenser is 1 bar (100 kPa) or less, preferably 0.5 bar (50 kPa) or less.

The terms "vaporizer," "stripping gas vaporizer," "stripper" and "product phase stripper" are used herein interchangeably, and refer to a separation device that employs stripping gas to aid in the separation of the components of the product-containing stream from the product.

As used herein, the term "average CO partial pressure" means the average carbon monoxide partial pressure determined at the vapor outlet of the vaporizer over at least a 10 minute period at steady state operation. Determining mole % of CO in a gas composition using gas chromatography (GC) is well known; CO partial pressure is then calculated by measuring total pressure and using Raoult's Law.

As used herein, the term "average $H_2$ partial pressure" means the average hydrogen partial pressure determined at the vapor outlet of the vaporizer over at least a 10 minute period at steady state operation. Determining mole % of $H_2$ in a gas composition using gas chromatography (GC) is well known; hydrogen partial pressure is then calculated by measuring total pressure and using Raoult's Law.

Hydrogen and carbon monoxide may be obtained from any suitable source, including petroleum cracking and refinery operations. Syngas mixtures are a preferred source of hydrogen and CO.

Syngas (from synthesis gas) is the name given to a gas mixture that contains varying amounts of CO and $H_2$. Production methods are well known. Hydrogen and CO typically are the main components of syngas, but syngas may contain $CO_2$ and inert gases such as $N_2$ and Ar. The molar ratio of $H_2$ to CO varies greatly but generally ranges from 1:100 to 100:1 and preferably between 1:10 and 10:1. Syngas is commercially available and is often used as a fuel source or as an intermediate for the production of other chemicals. The most preferred $H_2$:CO molar ratio for chemical production is between 3:1 and 1:3 and usually is targeted to be between about 1:2 and 2:1 for most hydroformylation applications.

The substituted or unsubstituted olefinic reactants that may be employed in the hydroformylation process include both optically active (prochiral and chiral) and non-optically active (achiral) olefinic unsaturated compounds containing from 2 to 40, preferably 3 to 30, carbon atoms, more preferably from 4 to 20 carbon atoms. These compounds are described in detail in U.S. Pat. No. 7,863,487. Such olefinic unsaturated compounds can be terminally or internally unsaturated and be of straight-chain, branched chain or cyclic structures, as well as olefin mixtures, such as obtained from the dimerization of mixed butenes, the oligomerization of propene, butene, isobutene, etc. (such as so called dimeric, trimeric or tetrameric propylene and the like, as disclosed, for example, in U.S. Pat. Nos. 4,518,809 and 4,528,403).

Prochiral and chiral olefins useful in the asymmetric hydroformylation can be employed to produce enantiomeric aldehyde mixtures. Illustrative optically active or prochiral olefinic compounds useful in asymmetric hydroformylation are described, for example, in U.S. Pat. Nos. 4,329,507, 5,360,938 and 5,491,266.

A solvent advantageously is employed in the hydroformylation process. Any suitable solvent that does not unduly interfere with the hydroformylation process can be used. By way of illustration, suitable solvents for rhodium catalyzed hydroformylation processes include those disclosed, for example, in U.S. Pat. Nos. 3,527,809; 4,148,830; 5,312,996; and 5,929,289. In rhodium catalyzed hydroformylation processes, it may be preferred to employ, as a primary solvent, aldehyde compounds corresponding to the aldehyde products desired to be produced and/or higher boiling aldehyde liquid condensation by-products, for example, as might be produced in situ during the hydroformylation process, as described for example in U.S. Pat. No. 4,148,380 and U.S. Pat. No. 4,247,486. The primary solvent will normally eventually comprise both aldehyde products and higher boiling aldehyde liquid condensation by-products ("heavies"), due to the nature of the continuous process. The amount of solvent is not especially critical and need only be sufficient to provide the reaction medium with the desired amount of transition metal concentration. Typically, the amount of solvent ranges from about 5 percent to about 95 percent by weight, based on the total weight of the reaction fluid. Mixtures of solvents may be employed.

Illustrative metal-organophosphorous ligand complexes employable in such hydroformylation reactions include metal-organophosphorous ligand complex catalysts. These catalysts, as well as methods for their preparation, are well known in the art and include those disclosed in the patents mentioned herein. In general, such catalysts may be pre-formed or formed in situ and comprise metal in complex combination with an organophosphorous ligand, carbon monoxide and optionally hydrogen. The exact structure of the catalyst is not known.

The metal-organophosphorous ligand complex catalyst can be optically active or non-optically active. The metals can include Group 8, 9 and 10 metals selected from rhodium (Rh), cobalt (Co), iridium (Ir), ruthenium (Ru), iron (Fe), nickel (Ni), palladium (Pd), platinum (Pt), osmium (Os) and mixtures thereof, with the preferred metals being rhodium, cobalt, iridium and ruthenium, more preferably rhodium, cobalt and ruthenium, especially rhodium. Mixtures of these metals may be used. The permissible organophosphorous ligands that make up the metal-organophosphorous ligand complexes and free organophosphorous ligand include mono-, di-, tri- and higher polyorganophosphorus ligands. Mixtures of ligands may be employed in the metal-organophosphorous ligand complex catalyst and/or free ligand, and such mixtures may be the same or different. In one embodiment of the invention, a mixture of monoorganophosphite and organopolyphosphite, e.g., bisphosphite, ligands can be employed.

The organophosphorous compounds that may serve as the ligand of the metal-organophosphorous ligand complex catalyst and/or free ligand may be of the achiral (optically inactive) or chiral (optically active) type and are well known in the art. Achiral organophosphorous ligands are preferred.

Among the organophosphorous ligands that may serve as the ligand of the metal-organophosphorous ligand complex catalyst are monoorganophosphite, diorganophosphite, triorganophosphite and organopolyphosphite compounds. Such organophosphorous ligands and methods for their preparation are well known in the art.

Representative monoorganophosphites may include those having the formula:

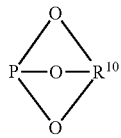
<<I>> wherein $R^{10}$ represents a substituted or unsubstituted trivalent hydrocarbon radical containing from 4 to 40 carbon atoms or greater, such as trivalent acyclic and trivalent cyclic radicals, e.g., trivalent alkylene radicals such as those derived from 1,2,2-trimethylolpropane and the like, or trivalent cycloalkylene radicals such as those derived from 1,3,5-trihydroxycyclohexane and the like. Such monoorganophosphites may be found described in greater detail, for example, in U.S. Pat. No. 4,567,306.

Representative diorganophosphites may include those having the formula:

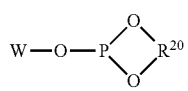
<<II>> wherein $R^{20}$ represents a substituted or unsubstituted divalent hydrocarbon radical containing from 4 to 40 carbon atoms or greater and W represents a substituted or unsubstituted monovalent hydrocarbon radical containing from 1 to 18 carbon atoms or greater.

Representative substituted and unsubstituted monovalent hydrocarbon radicals represented by W in the above Formula (II) include alkyl and aryl radicals, while representative substituted and unsubstituted divalent hydrocarbon radicals represented by $R^{20}$ include divalent acyclic radicals and divalent aromatic radicals. Illustrative divalent acyclic radicals include, for example, alkylene, alkylene-oxy-alkylene, alkylene-S-alkylene, cycloalkylene radicals, and, alkylene-$NR^{24}$-alkylene wherein $R^{24}$ is hydrogen or a substituted or unsubstituted monovalent hydrocarbon radical, e.g., an alkyl radical having 1 to 4 carbon atoms. The more preferred divalent acyclic radicals are the divalent alkylene radicals such as disclosed more fully, for example, in U.S. Pat. Nos. 3,415,906 and 4,567,302 and the like. Illustrative divalent aromatic radicals include, for example, arylene, bisarylene, arylene-alkylene, arylene-alkylene-arylene, arylene-oxy-arylene, arylene-$NR^{24}$-arylene wherein $R^{24}$ is as defined above, arylene-S-arylene, arylene-S-alkylene and the like. More preferably $R^{20}$ is a divalent aromatic radical such as disclosed more fully, for example, in U.S. Pat. Nos. 4,599,206, 4,717,775, 4,835,299, and the like.

Representative of a more preferred class of diorganophosphites are those of the formula:

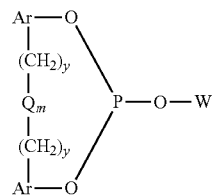
<<III>> wherein W is as defined above, each Ar is the same or different and represents a substituted or unsubstituted aryl radical, each y is the same or different and is a value of 0 or 1, Q represents a divalent bridging group selected from —$C(R^{33})_2$—, —O—, —S—, —$NR^{24}$—, $Si(R^{35})_2$ and —CO—, wherein each $R^{33}$ is the same or different and represents hydrogen, an alkyl radical having from 1 to 12 carbon atoms, phenyl, tolyl, and anisyl, $R^{24}$ is as defined above, each $R^{35}$ is the same or different and represents hydrogen or a methyl radical, and m has a value of 0 or 1. Such diorganophosphites are described in greater detail, for example, in U.S. Pat. Nos. 4,599,206, 4,717,775, and 4,835,299.

Representative triorganophosphites may include those having the formula:

<<IV>> wherein each $R^{46}$ is the same or different and is a substituted or unsubstituted monovalent hydrocarbon radical e.g., an alkyl, cycloalkyl, aryl, alkaryl and aralkyl radicals that may contain from 1 to 24 carbon atoms. Illustrative triorganophosphites include, for example, trialkyl phosphites, dialkylaryl phosphites, alkyldiaryl phosphites, triaryl phosphites, and the like, such as, for example, trimethyl phosphite, triethyl phosphite, butyldiethyl phosphite, dimethylphenyl phosphite, triphenyl phosphite, trinaphthyl phosphite, bis(3,6,8-tri-t-butyl-2-naphthyl)methylphosphite, bis(3,6,8-tri-t-butyl-2-naphthyl)cyclohexylphosphite, tris(3,6-di-t-butyl-2-naphthyl)phosphite, bis(3,6,8-tri-t-butyl-2-naphthyl)phenylphosphite, and bis(3,6,8-tri-t-butyl-2-naphthyl)(4-sulfonylphenyl)phosphite, and the like. The most preferred triorganophosphite is triphenylphosphite. Such triorganophosphites are described in greater detail, for example, in U.S. Pat. Nos. 3,527,809 and 5,277,532.

Representative organopolyphosphites contain two or more tertiary (trivalent) phosphorus atoms and may include those having the formula:

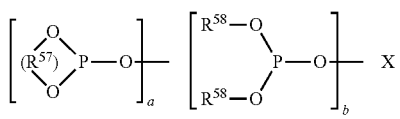
<<V>> wherein X represents a substituted or unsubstituted n-valent organic bridging radical containing from 2 to 40 carbon atoms, each $R^{57}$ is the same or different and represents a divalent organic radical containing from 4 to 40 carbon atoms, each $R^{58}$ is the same or different and represents a substituted or unsubstituted monovalent hydrocarbon radical containing from 1 to 24 carbon atoms, a and b can be the same or different and each have a value of 0 to 6, with the proviso that the sum of a+b is 2 to 6 and n equals a+b. It is to be understood that when a has a value of 2 or more, each $R^{57}$ radical may be the same or different. Each $R^{58}$ radical may also be the same or different in any given compound.

Representative n-valent (preferably divalent) organic bridging radicals represented by X and representative divalent organic radicals represented by $R^{57}$ above, include both acyclic radicals and aromatic radicals, such as alkylene, alkylene-$Q_m$-alkylene, cycloalkylene, arylene, bisarylene, arylene-alkylene, and arylene-$(CH_2)_y$-$Q_m$-$(CH_2)_y$-arylene radicals, and the like, wherein each Q, y and m are as defined above in Formula (III). The more preferred acyclic radicals represented by X and $R^{57}$ above are divalent alkylene radicals, while the more preferred aromatic radicals represented by X and $R^{57}$ above are divalent arylene and bisarylene radicals, such as disclosed more fully, for example, in U.S. Pat. Nos. 4,769,498; 4,774,361: 4,885,401; 5,179,055; 5,113,022; 5,202,297; 5,235,113; 5,264,616; 5,364,950 and 5,527,950. Representative preferred monovalent hydrocarbon radicals represented by each $R^{58}$ radical above include alkyl and aromatic radicals.

Illustrative preferred organopolyphosphites may include bisphosphites such as those of Formulas (VI) to (VIII) below:

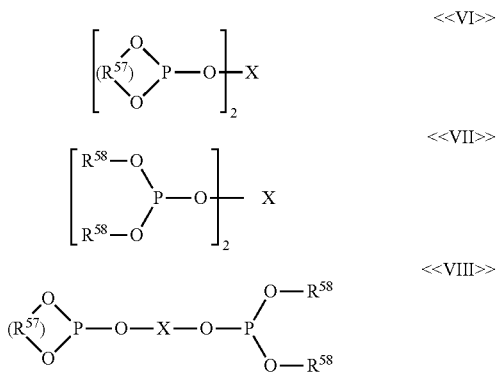

wherein each $R^{57}$, $R^{58}$ and X of Formulas (VI) to (VIII) are the same as defined above for Formula (V). Preferably each $R^{57}$ and X represents a divalent hydrocarbon radical selected from alkylene, arylene, arylene-alkylene-arylene, and bisarylene, while each $R^{58}$ radical represents a monovalent hydrocarbon radical selected from alkyl and aryl radicals. Organophosphite ligands of such Formulas (V) to (VIII) may be found disclosed, for example, in U.S. Pat. Nos. 4,668,651; 4,748,261; 4,769,498; 4,774,361; 4,885,401; 5,113, 022; 5,179,055; 5,202,297; 5,235,113; 5,254,741; 5,264,616; 5,312,996; 5,364,950; and 5,391,801.

$R^{10}$, $R^{20}$, $R^{46}$, $R^{57}$, $R^{58}$, Ar, Q, X, m, and y in Formulas (VI) to (VIII) are as defined above. Most preferably X represents a divalent aryl-$(CH_2)_y$-$(Q)_m$-$(CH_2)_y$-aryl radical wherein each y individually has a value of 0 or 1; m has a value of 0 or 1 and Q is —O—, —S— or —$C(R^{35})_2$— where each $R^{35}$ is the same or different and represents hydrogen or a methyl radical. More preferably each alkyl radical of the above defined $R^{58}$ groups may contain from 1 to 24 carbon atoms and each aryl radical of the above-defined Ar, X, $R^{57}$ and $R^{58}$ groups of the above Formulas (VI) to (VIII) may contain from 6 to 18 carbon atoms and said radicals may be the same or different, while the preferred alkylene radicals of X may contain from 2 to 18 carbon atoms and the preferred alkylene radicals of $R^{57}$ may contain from 5 to 18 carbon atoms. In addition, preferably the divalent Ar radicals and divalent aryl radicals of X of the above formulas are phenylene radicals in which the bridging group represented by —$(CH_2)_y$-$(Q)_m$—$(CH_2)_y$— is bonded to said phenylene radicals in positions that are ortho to the oxygen atoms of the formulas that connect the phenylene radicals to their phosphorus atom of the formulae. It is also preferred that any substituent radical when present on such phenylene radicals be bonded in the para and/or ortho position of the phenylene radicals in relation to the oxygen atom that bonds the given substituted phenylene radical to its phosphorus atom.

Any of the $R^{10}$, $R^{20}$, $R^{57}$, $R^{58}$, W, X, Q and Ar radicals of such organophosphites of Formulas (I) to (VIII) above may be substituted if desired, with any suitable substituent containing from 1 to 30 carbon atoms that does not unduly adversely affect the desired result of the process of this invention. Substituents that may be on said radicals in addition to corresponding hydrocarbon radicals such as alkyl, aryl, aralkyl, alkaryl and cyclohexyl substituents, may include for example silyl radicals such as —$Si(R^{35})_3$; amino radicals such as —$N(R^{15})_2$; phosphine radicals such as -aryl-$P(R^{15})_2$; acyl radicals such as —$C(O)R^{15}$ acyloxy radicals such as —$OC(O)R^{15}$; amido radicals such as —$CON(R^{15})_2$ and —N—$(R^{15})COR^{15}$; sulfonyl radicals such as —$SO_2 R^{15}$, alkoxy radicals such as —$OR^{15}$; sulfinyl radicals such as —$SOR^{15}$, phosphonyl radicals such as —$P(O)(R^{15})_2$, as well as halo, nitro, cyano, trifluoromethyl, hydroxy radicals and the like, wherein each $R^{15}$ radical individually represents the same or different monovalent hydrocarbon radical having from 1 to 18 carbon atoms (e.g., alkyl, aryl, aralkyl, alkaryl and cyclohexyl radicals), with the proviso that in amino substituents such as —$N(R^{15})_2$ each $R^{15}$ taken together can also represent a divalent bridging group that forms a heterocyclic radical with the nitrogen atom, and in amido substituents such as —$C(O)N(R^{15})_2$ and —$N(R^{15})COR^{15}$ each $R^{15}$ bonded to N can also be hydrogen. It is to be understood that any of the substituted or unsubstituted hydrocarbon radicals groups that make up a particular given organophosphite may be the same or different.

More specifically illustrative substituents include primary, secondary and tertiary alkyl radicals such as methyl, ethyl, n-propyl, isopropyl, butyl, sec-butyl, t-butyl, neopentyl, n-hexyl, amyl, sec-amyl, t-amyl, iso-octyl, decyl, octadecyl, and the like; aryl radicals such as phenyl, naphthyl, and the like; aralkyl radicals such as benzyl, phenylethyl, triphenylmethyl, and the like; alkaryl radicals such as tolyl, xylyl, and the like; alicyclic radicals such as cyclopentyl, cyclohexyl, 1-methylcyclohexyl, cyclooctyl, cyclohexylethyl, and the like; alkoxy radicals such as methoxy, ethoxy, propoxy, t-butoxy, —$OCH_2CH_2OCH_3$, —$O(CH_2 CH_2)_2OCH_3$, —$O(CH_2CH_2)_3OCH_3$, and the like; aryloxy radicals such as phenoxy and the like; as well as silyl radicals such as —$Si(CH_3)_3$, —$Si(OCH_3)_3$, —$Si(C_3H_7)_3$, and the like; amino radicals such as —$NH_2$, —$N(CH_3)_2$, —$NHCH_3$, —$NH(C_2H_5)$, and the like; arylphosphine radicals such as —$P(C_6H_5)_{29}$ and the like; acyl radicals such as —$C(O)CH_3$, —$C(O)C_2H_5$, —$C(O)C_6H_5$, and the like; carbonyloxy radicals such as —C(O)OCH$_3$, and the like; oxycarbonyl radicals such as —O(CO)C$_6$H$_5$ and the like; amido radicals such as —CONH$_2$, —CON(CH$_3$)$_2$, —NHC(O)CH$_3$, and the like; sulfonyl radicals such as —S(O)$_2$C$_2$H$_5$ and the like; sulfinyl radicals such as —S(O)CH$_3$ and the like; sulfidyl radicals such as —SCH$_3$, —SC$_2$H$_5$, —SC$_6$H$_5$, and the like; phosphonyl radicals such as —P(O)(C$_6$H$_5$)$_2$, —P(O)(CH$_3$)$_2$, —P(O)(C$_2$H$_5$)$_2$, —P(O)(C$_3$H$_7$)$_2$, —P(O)(C$_4$H$_9$)$_2$, —P(O)(C$_6$H$_{13}$)$_2$, —P(O)CH$_3$(C$_6$H$_5$), —P(O)(H)(C$_6$H$_5$), and the like.

Specific illustrative examples of such organophosphite ligands include the following: tris(2,4-di-t-butylphenyl) phosphite, 2-t-butyl-4-methoxyphenyl(3,3'-di-t-butyl-5,5'-dimethoxy-1,1'-biphenyl-2,2'-diyl)phosphite, methyl(3,3'-di-t-butyl-5,5'-dimethoxy-1,1'-biphenyl-2,2'-diyl)phosphite, 6,6'-[[3,3'-bis(1,1-dimethylethyl)-5,5'-dimethoxy-[1,1'-biphenyl]-2,2'-diyl]bis(oxy)]bis-dibenzo[d,f][1,3,2]dioxaphosphepin, 6,6'-[[3,3',5,5'-tetrakis(1,1-dimethylethyl)-1,1'-biphenyl]-2,2'-diyl]bis(oxy)]bis-dibenzo[d,f][1,3,2]-dioxaphosphepin, (2R,4R)-di[2,2'-(3,3',5,5'-tetrakis-tert-butyl-1,1-biphenyl)]-2,4-pentyldiphosphite, (2R, 4R)di[2,2'-(3,3'-di-tert-butyl-5,5'-dimethoxy-1,1'-biphenyl)]-2,4-pentyldiphosphite, 2-[[2-[[4,8,-bis(1,1-dimethylethyl), 2,10-dimethoxydibenzo-[d,f][1,3,2]dioxophosphepin-6-yl]oxy]-3-(1,1-dimethylethyl)-5-methoxyphenyl]methyl]-4-methoxy, methylenedi-2,1-phenylene tetrakis[2,4-bis(1,1-dimethylethyl)phenyl]ester of phosphorous acid, and [1,1'-biphenyl]-2,2'-diyl tetrakis[2-(1,1-dimethylethyl)-4-methoxyphenyl]ester of phosphorous acid.

In one embodiment, the organophosphite ligand comprises an organobisphosphite ligand. In one embodiment, the ligand is a bidentate phosphoramidite ligand, such as a bidentate phosphoramidite ligand of the class disclosed in, e.g., WO 00/56451 A1.

The metal-organophosphorous ligand complex catalysts may be in homogeneous or heterogeneous form. For instance, preformed rhodium hydrido-carbonyl-organophosphorous ligand catalysts may be prepared and introduced into a hydroformylation reaction mixture. More preferably, the rhodium-organophosphorous ligand complex catalysts can be derived from a rhodium catalyst precursor that may be introduced into the reaction medium for in situ formation of the active catalyst. For example, rhodium catalyst precursors such as rhodium dicarbonyl acetylacetonate, Rh$_2$O$_3$, Rh$_4$(CO)$_{12}$, Rh$_6$(CO)$_{16}$, Rh(NO$_3$)$_3$, and the like may be introduced into the reaction mixture along with the organophosphorous ligand for the in situ formation of the active catalyst. In a preferred embodiment, rhodium dicarbonyl acetylacetonate is employed as a rhodium precursor and reacted in the presence of a solvent with the organophosphorous ligand to form a catalytic rhodium-organophosphorous ligand complex precursor that is introduced into the reactor along with excess (free) organophosphorous ligand for the in situ formation of the active catalyst. In any event, it is sufficient that carbon monoxide, hydrogen and the organophosphorous ligand are all ligands that are capable of being complexed with the metal and that an active metal-organophosphorous ligand catalyst is present in the reaction mixture under the conditions used in the hydroformylation reaction. Carbonyl and organophosphorous ligands may be complexed to the rhodium either prior to or in situ during the hydroformylation process.

By way of illustration, a preferred catalyst precursor composition consists essentially of a solubilized rhodium carbonyl organophosphite ligand complex precursor, a solvent and, optionally, free organophosphite ligand. The preferred catalyst precursor composition can be prepared by forming a solution of rhodium dicarbonyl acetylacetonate, an organic solvent and a organophosphite ligand. The organophosphorous ligand readily replaces one of the carbonyl ligands of the rhodium acetylacetonate complex precursor as witnessed by the evolution of carbon monoxide gas.

Accordingly, the metal-organophosphorus ligand complex catalyst advantageously comprises the metal complexed with carbon monoxide and an organophosphorous ligand, said ligand being bonded (complexed) to the metal in a chelated and/or non-chelated fashion.

Mixtures of catalysts can be employed. The amount of metal-organophosphorous ligand complex catalyst present in the reaction fluid need only be that minimum amount necessary to provide the given metal concentration desired to be employed and that will furnish the basis for at least the catalytic amount of metal necessary to catalyze the particular hydroformylation process involved such as disclosed, for example, in the above-mentioned patents. In general, catalytic metal, e.g., rhodium, concentrations in the range of from 10 ppmw to 1000 ppmw, calculated as free metal in the reaction medium, should be sufficient for most processes, while it is generally preferred to employ from 10 to 500 ppmw of metal, and more preferably from 25 to 350 ppmw of metal.

In addition to the metal-organophosphorous ligand complex catalyst, free organophosphorous ligand (i.e., ligand that is not complexed with the metal) may also be present in the reaction medium. The free organophosphorous ligand may correspond to any of the above-defined organophosphorous ligands discussed above. It is preferred that the free organophosphorous ligand be the same as the organophosphorous ligand of the metal-organophosphorous ligand complex catalyst employed. However, such ligands need not be the same in any given process. The hydroformylation process of this invention may involve from 0.1 moles or less to 100 moles or higher of free organophosphorous ligand per mole of metal in the reaction medium. Preferably, the hydroformylation process is carried out in the presence of from 1 to 50 moles of organophosphorous ligand per mole of metal present in the reaction medium. More preferably, for organopolyphosphites, from 1.1 to 4 moles of organopolyphosphite ligand are employed per mole of metal. Said amounts of organophosphorous ligand are the sum of both the amount of organophosphorous ligand that is bound (complexed) to the metal present and the amount of free organophosphorous ligand present. If desired, additional organophosphorous ligand can be supplied to the reaction medium of the hydroformylation process at any time and in any suitable manner, e.g., to maintain a predetermined level of free ligand in the reaction medium.

The use of an aqueous buffer solution, such as in an extraction system, to prevent and/or lessen hydrolytic degradation of an organophosphite ligand and deactivation of a metal-organophosphite ligand complex is well-known and is disclosed, e.g., in U.S. Pat. No. 5,741,942 and U.S. Pat. No. 5,741,944. Mixtures of buffers may be employed.

Optionally, an organic nitrogen compound may be added to the hydroformylation reaction fluid to scavenge the acidic hydrolysis by-products formed upon hydrolysis of the organophosphorous ligand, as taught, for example, in U.S. Pat. No. 4,567,306 and U.S. Pat. No. 5,731,472. Such organic nitrogen compounds may be used to react with and to neutralize the acidic compounds by forming conversion product salts therewith, thereby preventing the catalytic metal from complexing with the acidic hydrolysis by-products and thus helping to protect the activity of the catalyst while it is present in the reaction zone under reaction conditions.

The hydroformylation process, and conditions for its operation, are well known. The hydroformylation process may be asymmetric or non-asymmetric, the preferred process being non-asymmetric, and may be conducted in any batch, continuous or semi-continuous fashion and may involve any catalyst liquid and/or gas recycle operation desired.

The hydroformylation reaction conditions employed will be governed by the type of aldehyde product desired. For instance, the total gas pressure of hydrogen, carbon monoxide and olefin starting compound of the hydroformylation process may range from 1 to 69,000 kPa. In general, however, it is preferred that the process be operated at a total gas pressure of hydrogen, carbon monoxide and olefin starting compound of less than 14,000 kPa and more preferably less than 3,400 kPa. The minimum total pressure is limited predominantly by the amount of reactants necessary to obtain a desired rate of reaction. More specifically, the carbon monoxide partial pressure of the hydroformylation process is preferably from 1 to 6,900 kPa, and more preferably from 21 to 5,500 kPa, while the hydrogen partial pressure is preferably from 34 to 3,400 kPa and more preferably from 69 to 2,100 kPa. In general, the molar ratio of gaseous $H_2$:CO may range from 1:10 to 100:1 or higher, the more preferred molar ratio being from 1:10 to 10:1.

In general, the hydroformylation process may be conducted at any operable reaction temperature. Advantageously, the hydroformylation process is conducted at a reaction temperature from −25° C. to 200° C., preferably from 50° C. to 120° C.

The hydroformylation process may be carried out using one or more suitable reactors such as, for example, a fixed bed reactor, a fluid bed reactor, a continuous stirred tank reactor (CSTR) or a slurry reactor. The optimum size and shape of the catalysts will depend on the type of reactor used. The reaction zone employed may be a single vessel or may comprise two or more discrete vessels.

The hydroformylation process of this invention may be conducted in one or more steps or stages. The exact number of reaction steps or stages will be governed by the best compromise between capital costs and achieving high catalyst selectivity, activity, lifetime and ease of operability, as well as the intrinsic reactivity of the starting materials in question and the stability of the starting materials and the desired reaction product to the reaction conditions.

In one embodiment, the hydroformylation process useful in this invention may be carried out in a multistaged reactor such as described, for example, in U.S. Pat. No. 5,728,893. Such multistaged reactors can be designed with internal, physical barriers that create more than one theoretical reactive stage per vessel.

It is generally preferred to carry out the hydroformylation process in a continuous manner. Continuous hydroformylation processes are well known in the art; the most preferred hydroformylation process comprises a continuous liquid catalyst recycle process. Suitable liquid catalyst recycle procedures are disclosed, for example, in U.S. Pat. Nos. 4,668,651; 4,774,361; 5,102,505 and 5,110,990.

FIG. 1 illustrates an integrated hydroformylation process of the invention. With reference to FIG. 1, an olefin feed stream 1 comprising one or more olefinic compounds and optionally one or more inert lights is fed into a hydroformylation reactor system 100 comprising one or more hydroformylation reactors (Oxo reactors). Concurrently, a gaseous feed stream 2 comprising carbon monoxide, hydrogen and optionally one or more gaseous inerts is also fed into the hydroformylation reactor system 100. For the sake of simplicity, the hydroformylation reactor system is shown in FIG. 1 as a single unit, but it advantageously comprises a series of sequentially-connected hydroformylation reactors.

A recycle catalyst stream 23, which comprises a transition metal-organomonophosphite ligand complex catalyst, preferably, a rhodium-organomonophosphite ligand complex catalyst, and optionally free or uncomplexed organomonophosphite ligand, solubilized and dissolved in a liquid heavy by-products phase is also fed into the hydroformylation reactor system 100, wherein hydroformylation of the olefin occurs to produce a crude hydroformylation product stream 21 comprising one or more aldehyde products, one or more heavy by-products, one or more unconverted olefinic reactants, the transition metal-organophosphite ligand complex catalyst, free organophosphite ligand, and lights including inert lights, carbon monoxide, and optionally hydrogen. In one embodiment of the invention, the crude hydroformylation product stream 21 is a stream comprising liquid and gas, which gas may be partially dissolved in the liquid. A reactor vent stream 27 comprising primarily light components, including inert lights, hydrogen, and carbon monoxide, can be taken overhead as a gaseous stream from the reactor system 100 from any one or more of the reactors therein. An optional flash pot (not shown) in stream 21 may be used to reduce pressure and remove excess $H_2$.

The liquid hydroformylation product stream 21 is fed into a stripping gas vaporizer unit 200, from which an overhead gas stream 22 is obtained comprising one or more aldehyde products, one or more unconverted olefinic reactants, a portion of the heavy by-products, and lights including one or more inert lights, carbon monoxide, and optionally hydrogen. The overhead gas stream 22 from the stripping gas vaporizer is fed into a product condenser 300 from which a condenser overhead gas stream 28 is obtained comprising a portion of the one or more olefinic reactants, and a portion of the inert lights, carbon monoxide, and optionally hydrogen. From the condenser 300 a liquid product stream 26 is obtained comprising one or more aldehyde products, the portion of heavy by-products from the overhead gas stream from the vaporizer, and the balance of the unconverted olefinic reactant(s). The condenser overhead gas stream 28 is split into a recycle stream 24, which is sent back to the stripping gas vaporizer 200 via blower 400, and a stream 25 that can be recycled to the hydroformylation reactor system 100, or flared, or used as a fuel, or used in another downstream process. The recycle stream 24 comprises one or more unconverted olefin reactants and lights including one or more inert lights, carbon monoxide, and optionally hydrogen and is sent to blower 400. Stream 25 comprises one or more unconverted olefin reactants and lights including one or more inert lights, carbon monoxide, and optionally hydrogen. From the stripping gas vaporizer 200, a recycle catalyst stream 23 is obtained as a vaporizer tails stream comprising the balance of the heavy by-products, the transition metal-organophosphite ligand complex catalyst, and optionally, free organophosphite ligand. Recycle catalyst stream 23 is recycled as a liquid catalyst stream back to the Oxo reactor system 100.

Stream 55 can be used to add CO directly to vaporizer 200 and/or anywhere in stream 24 prior to entry into the vaporizer 200 via stream 20. The CO partial pressure in the vaporizer can be measured directly in the vaporizer or indirectly by analyzing one or more appropriate vaporizer input and/or output streams such as, for example, an appropriate selection of streams 20, 22, 24, 25, 55 and/or 28.

Without the addition of CO, the partial pressure of CO in the overhead gas recycle stream will vary as a function of the operating temperature of the condenser 300. In such a case, manipulation of the operating temperature of the condenser 300 provides little control over the desired quantity of CO to be recycled to the vaporizer 200 for stabilization of the hydroformylation catalyst and does not provide a sufficient amount of CO to reach the desired, e.g., greater than 16 psia (110 kPa) to 50 psia (345 kPa), CO partial pressure. Thus, one feature of the invention is the addition of CO to the vaporizer 200, e.g., via line 55 as shown in FIG. 1.

A substantial amount of the CO added via line 55 will be recycled via line 24 depending on the line 24/line 25 split ratio. This recycling reduces the total amount of flow from line 55 needed to maintain the CO partial pressure in the stripping gas vaporizer as compared to conventional vaporizers due to the relatively low solubility of CO in the liquid product outlet streams. The flow of line 55 is regulated to maintain the observed CO partial pressure in the vaporizer within the desired ranges. This line can also be used to introduce CO-containing stripping gas during startup where suitable gas from the upstream process may not be available. In various embodiments of the invention, streams equivalent to stream 55 may be added anywhere in the vaporizer. However, it is preferred to introduce CO to the vaporizer by mixing the make-up CO feed stream with the stripping gas 24 prior to entry into the vaporizer as stream 20.

Stream 55 advantageously is a CO-containing stream, and preferably is substantially free of sulfur- or halide-containing impurities and oxygen ($O_2$). The source of stream 55 may be the same source as the source of CO and $H_2$ to the hydroformylation reaction zone, but is preferably enriched in CO using conventional techniques such as pressure swing adsorption, membrane separation, or other known technologies. These concentration technologies may be fed with fresh syngas and/or one of the vents from the hydroformylation unit. In general, the higher the CO content in stream 55, the smaller the flow of vent stream 25 which results in lower vent losses.

The reaction fluid from the hydroformylation reactors can be fed directly into the stripping gas vaporizer. A stripping gas vaporizer is shown in FIG. 1 as a single unit 200, but the vaporizer may comprise a series of sequentially-connected vaporizers that operate at different pressures.

Alternatively, the reaction fluid can be fed first into a flash vessel to let down pressure and remove reactive and inert lights, after which the remaining liquid can be fed to the stripping gas vaporizer. For example, a flash vessel, operating at a pressure in-between the reactor (100) pressure and the vaporizer (200) pressure, enables the removal of gases such as hydrogen, $CO_2$, methane, nitrogen, argon, and the like before they enter the vaporizer. This not only allows the concentration of these gases to be rapidly lowered, but helps prevent them from accumulating in the recycled stripping gas. Accumulation of such gases would require a higher fresh CO feed rate (stream 55) and purge flow rate (stream 25) in order to achieve the desired CO partial pressure in the vaporizer. Thus using a flash vessel prior to the vaporizer can extend the viable operating pressure of the vaporizer (i.e., allows for a lower total pressure) and may result in more economical operation.

The composition of the reaction fluid from the hydroformylation reactor, exclusive of the transition metal-organophosphorous ligand complex catalyst and any free ligand, advantageously comprises from about 38 to about 58 weight percent of one or more aldehyde products, from about 16 to about 36 weight percent heavies by-products, from about 2 to about 22 weight percent unconverted olefinic reactants, from about 1 to about 22 weight percent inert lights, from about 0.02 to about 0.5 weight percent carbon monoxide, and less than about 100 ppmw hydrogen, the total adding up to 100 weight percent.

The vaporizer hardware may be conventional in design, and many examples are known to the skilled person. The vaporizer is advantageously designed to include a vertical series of tubes within a heat exchanger. Optimum vaporizer dimensions (number of tubes, diameter and length) are determined by the plant capacity, and can be readily determined by one skilled in the art. Examples of vaporizers and their use are described in U.S. Pat. No. 8,404,903.

In order to maintain the CO partial pressure of the invention, it may be necessary to discharge a portion of the recycled stripping gas by means of a vent stream 25. The aldehyde, unreacted olefins and alkanes entrained in the vent stream can be recovered by condensation. The condensation can be conducted in any suitable condenser using any suitable heat transfer fluid. Examples of such fluids include, e.g., chilled water, brine or other salt solutions, DOWTHERM brand heat transfer fluid, or other heat exchange fluids, including mixtures thereof.

Since the stripping gas vaporizer and the product condenser can be operated at essentially constant pressure, no extensive compression of gaseous streams is required in some embodiments of the inventive process. A blower or fan can be suitably used for the circulation of the recycle gas from the product condenser to the stripper. Compared to a compression unit, a blower or fan involves considerably less capital expense and maintenance expense; however, a compression unit can be used if desired. Generally, the stripper and product condenser are operated at a pressure in the range of from 1.5 bar absolute (150 kPa) to 4 bar absolute (400 kPa), preferably from 2 to 3 bar absolute (200-300 kPa).

The CO partial pressure in the stripping gas vaporizer advantageously is maintained within the range of greater than 16 psia (110 kPa) to 50 psia (345 kPa) by adding a CO-containing stream, e.g., as shown in FIG. 1 via line 55. In one embodiment of the invention, the vaporizer is operated at a temperature that is high enough to remove at least a portion of the heavies from the product fluid in the gas overhead stream, yet low enough to ensure stability of the catalyst and organophosphorous ligand in the vaporizer. Preferably, the vaporizer process outlet temperature is at least 80° C., and more preferably is at least 90° C. Preferably, the vaporizer process outlet temperature is not more than 130° C., and more preferably is not more than 120° C. The vaporizer total pressure advantageously is greater at least 16 psia (110 kPa), and preferably is at least 20 psia (138 kPa), and most preferably is at least 25 psia (172 kPa). The vaporizer total pressure is advantageously not more than 100 psia (689 kPa), and preferably is not more than 60 psia (414 kPa). The CO partial pressure is greater than 16 psia (110 kPa), preferably greater than 20 psia (138 kPa) and most preferably above 25 psia (172 kPa). There is no advantage to CO partial pressure above 50 psia (345 kPa) as this necessitates higher vaporizer temperatures to maintain productivity; thus, it is preferred that the CO partial pressure be no more than 50 psia (345 kPa), preferably less than 40 psia (276 kPa) and more preferably less than 35 psia (241 kPa). The vaporizer advantageously operates with a mass ratio of crude liquid product feed to liquid tails ranging from 1.5/1 to 5/1, preferably, from 2/1 to 3/1. The mass ratio of crude liquid product feed to recycle gas feed to the vaporizer is preferably greater than 0.1/1, more preferably greater than 0.25/1, but preferably less than 2/1, and more preferably less than 1/1. In one embodiment of the invention, in the vaporizer, the $H_2$ partial pressure is from 0.1 psia (0.7 kPa), or from 3 psia (21 kPa), to less than half the CO partial pressure. In one embodiment, the invention is a process as described herein wherein the stripping gas vaporizer and the product condenser are operated essentially isobarically.

The overhead gas stream from the vaporizer is fed into a condenser. Any cooling medium desired can be employed with the condenser, and the type of cooling medium is not particularly critical. In one embodiment of the invention, the condenser employs conventional water cooling. Water is the preferred cooling medium at an operating temperature ranging from above freezing (i.e., greater than 0° C.) to about 50° C., preferably, from about 34° C. to about 45° C.

The overhead stream from the condenser advantageously is split into a gas vent stream and a gas recycle stream to the vaporizer. In one embodiment of the invention, the gas recycle stream from the condenser to the vaporizer comprises less than 5 weight percent of aldehyde products.

The use of syngas containing roughly 50 mol % $H_2$ increases the total pressure of the vaporizer, thus purified CO is preferred. If syngas is used, it need not be at the same $H_2$/CO ratio as syngas fed to the hydroformylation unit, since little of this syngas will be present in stream 23 to be recycled back to the hydroformylation system. A preferred source of this CO-containing stream 55 is a reactor vent stream that has been passed through a condenser to remove most of the condensables, such as aldehyde product and olefin starting materials, optionally in conjunction with a membrane separator or other separation device to further enrich the stream with CO.

In one embodiment, the invention is a continuous process comprising: (a) contacting CO, $H_2$, an olefin and a catalyst comprising a rhodium and a organophosphite ligand, preferably a monoorganophosphite ligand, in a reactor under hydroformylation reaction conditions to produce an aldehyde product; (b) removing a liquid product-containing stream from the reactor; (c) sending the liquid product-containing stream to a vaporizer; (d) introducing to the vaporizer a gas phase stream comprising CO; (e) separating the liquid product-containing stream in the vaporizer to produce a catalyst-containing liquid stream and a gas phase stream; and (f) maintaining an average CO partial pressure in the vaporizer of greater than 16 psia (110 kPa), preferably at least 17 psia (117 kPa).

Advantageously, the process of the invention results in lower rhodium loss and thereby lower catalyst costs compared to a comparative process that does not maintain the indicated CO partial pressure. In one embodiment of the invention, the crude product stream is obtained by contacting CO, $H_2$, an olefin and a catalyst comprising rhodium and an organophosphite ligand in a reaction zone under hydroformylation reaction conditions to produce an aldehyde product in a crude product stream. In one embodiment of the invention, the process further comprises removing, as a tails stream from the vaporizer, a liquid recycle catalyst stream comprising the transition metal-organophosphite ligand complex catalyst and heavy by-products.

In one embodiment, the invention provides a means of removing the product in a liquid recycle hydroformylation process comprising: (a) feeding a crude product stream comprising one or more products, one or more heavy by-products, a transition metal-organophosphite ligand complex catalyst, one or more unconverted reactants, and one or more inert lights into a stripping gas vaporizer; (b) removing from the vaporizer an overhead gas stream comprising one or more of the products, one or more unconverted reactants, one or more inert lights, and a portion of the heavy by-products, (c) feeding the overhead gas stream into a condenser; (d) removing from the condenser an overhead gas stream comprising one or more unconverted reactants and one or more inert lights, (e) recycling a portion of the condenser overhead gas steam to the vaporizer; and (f) removing, as a tails stream from the vaporizer, a liquid recycle catalyst stream comprising the catalyst and the balance of the heavy by-products, wherein the CO partial pressure in the vaporizer is maintained at an average value of from 17 psia (117 kPa) to 50 psia (345 kPa).

In one embodiment, the invention provides for an integrated process of hydroformylation, catalyst-product separation, and controlling heavy by-products in a catalyst recycle stream, the process comprising: (a) contacting a hydroformylation feed stream comprising one or more olefinic reactants and one or more inert lights with CO and hydrogen in the presence of a transition metal-organophosphite ligand complex catalyst and, optionally, free organophosphite ligand, under hydroformylation conditions sufficient to prepare a crude liquid hydroformylation product stream comprising one or more aldehyde products, one or more heavy by-products, a transition metal-organophosphite ligand complex catalyst, optionally, free organophosphite ligand, one or more unconverted olefinic reactants, and lights including one or more inert lights, carbon monoxide and, optionally, hydrogen; (b) feeding the crude liquid hydroformylation product stream into a stripping gas vaporizer; (c) removing from the stripping gas vaporizer an overhead gas stream comprising one or more aldehyde products, one or more unconverted olefinic reactants, a portion of the one or more heavy by-products, and lights including one or more inert lights, carbon monoxide, and optionally hydrogen; and feeding the vaporizer overhead gas stream into a condenser; (d) removing from the condenser an overhead gas stream comprising one or more unconverted olefinic reactants and lights including one or more inert lights, carbon monoxide, and optionally hydrogen; (e) recycling a portion of the condenser overhead gas stream to the vaporizer; and (f) removing as a tails stream from the vaporizer a liquid recycle catalyst stream comprising the balance of heavy by-products, the transition metal-ligand complex catalyst, and optionally free organophosphite ligand, and recycling the liquid recycle catalyst stream to step (a) wherein the CO partial pressure in the condenser overhead gas stream in step (c) is from 17 psia (117 kPa) to 50 psia (345 kPa).

Illustrative non-optically active aldehyde products include e.g., propionaldehyde, n-butyraldehyde, isobutyraldehyde, n-valeraldehyde, 2-methyl 1-butyraldehyde, hexanal, hydroxyhexanal, 2-methyl 1-heptanal, nonanal, 2-methyl-1-octanal, decanal, adipaldehyde, 2-methylglutaraldehyde, 2-methyladipaldehyde, 3-hydroxypropionaldehyde, 6-hydroxyhexanal, alkenals, e.g., 2-, 3- and 4-pentenal, alkyl 5-formylvalerate, 2-methyl-1-nonanal, 2-methyl 1-decanal, 3-propyl-1-undecanal, pentadecanal, 3-propyl-1-hexadecanal, eicosanal, 2-methyl-1-tricosanal, pentacosanal, 2-methyl-1-tetracosanal, nonacosanal, 2-methyl-1-octacosanal, hentriacontanal, 2-methyl-1-triacontanal, and the like.

Illustrative optically active aldehyde products include (enantiomeric) aldehyde compounds prepared by the asymmetric hydroformylation process of this invention such as, e.g., S-2-(p-isobutylphenyl)-propionaldehyde, S-2-(6-methoxy-2-naphthyl)propionaldehyde, S-2-(3-benzoylphenyl)-propionaldehyde, S-2-(3-fluoro-4-phenyl)phenylpropionaldehyde, and S-2-(2-methylacetaldehyde)-5-benzoylthiophene.

SPECIFIC EMBODIMENTS OF THE INVENTION

All parts and percentages in the following examples are by weight unless otherwise indicated. Pressures in the following examples are given as absolute pressure unless otherwise indicated. All manipulations such as preparation of catalyst solutions are done under inert atmosphere unless otherwise indicated. Comparative Experiments are not embodiments of the invention.

Rhodium analyses are performed by air/acetylene atomic absorption (AA) or by inductively coupled plasma (ICP). It has been found that air/acetylene AA will not reliably quantify clustered rhodium, but nonetheless, this method can still be used to indicate "rhodium loss" (e.g., the rhodium is clustered or otherwise no longer in solution). ICP is believed to detect all rhodium in the sample regardless of form due to the high temperature of the plasma, thus a decline in rhodium as measured by ICP indicates that a portion of the rhodium is no longer in solution. Color change (starting from a colorless or light yellow solution), darkening or formation of black film or solids is also indicative of catalyst degradation.

Gas compositions (mole %) are measured by gas chromatography (GC) and partial pressures are then calculated based on the total pressure using Raoult's law. It should be understood that the strip gas typically includes trace components in addition to those listed (e.g. ≤0.5 psia).

General Procedure

Unless otherwise indicated, examples and comparative experiments are conducted in 90 mL flow-through Fisher Porter reactors equipped with means for accurate control of temperatures and gas flows. Reactor off gases are analyzed by online GC to determine partial pressures. Mixing in the flow-through reactor is effected by continuous gas flow via a sparger at the bottom of the reactor. This reactor design is described in detail in U.S. Pat. No. 5,731,472, the teachings of which are incorporated by reference.

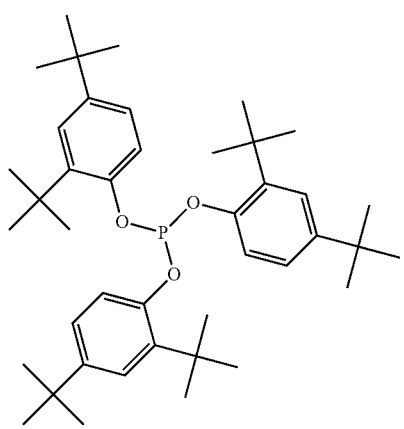

Ligand A

In a typical experiment, a solvent (TEXANOL or tetraglyme) is added to the assembled reactor under nitrogen at reaction temperature. A stock solution of Ligand A in toluene is then added, followed by a stock solution of rhodium prepared from dicarbonyl-acetylacetonato-rhodium in toluene. A 1:1 CO: $H_2$ mixture is passed through the liquid in the reactor at 165 psia (1138 kPa) for 30-60 minutes at 110° C. to form the rhodium-ligand complex. Adjustments to the reactor partial pressures are then made; the reactors are subsequently sealed and maintained at temperature without agitation.

Comparative Experiment A—not an Embodiment of the Invention

An experiment is conducted in the equipment of the General Procedure to simulate "vaporizer conditions" by heating a Texanol solution comprising 300 ppm rhodium and 10 molar equivalents of ligand A in a reactor at 110° C. under nitrogen (total pressure 165 psia; (1138 kPa)) with no syngas or olefin. These conditions will be used in subsequent experiments as the model for a typical vaporizer. The results are as follows:

| Initial [Rh] (ppm) | % of original rhodium by AA after | | | final solution appearance |
|---|---|---|---|---|
| | 2 days | 7 days | 10 days | |
| C. E. A  300 | 86 | 76 | 73 | dark brown with precipitate |

Under these conditions, the catalyst rapidly decomposes, starting as a clear yellow solution then changing to a dark solution with a dark precipitate and substantial loss of dissolved rhodium.

Examples 1-3 and C.E. B & C

Following the General Procedure, solutions of 525 ppm rhodium and 6 equivalents of Ligand A in tetraglyme are charged to individual reactors. Following the 30-60 minute contact with 1:1 CO:$H_2$ gas, Comparative Experiment B (C.E. B) is flushed with nitrogen for about 60 minutes, then sealed at 165 psia (1138 kPa). The remaining reactors are flushed with CO for about 60 minutes and then sealed under the pressures shown in Table 1. After 7 days, the reactors are sampled to determine rhodium loss, and the results are summarized in Table 1.

TABLE 1

Examining the effect of CO at various low pressures; rhodium accountability at 110° C.

| | CO psia (kPa) | % original Rh after | | Appearance |
|---|---|---|---|---|
| | | 2 days | 7 days | |
| C. E. B | 0 | 14.0 | 12.0 | black film and dark ppt |
| C. E. C | 15.7 (108.2) | 78.5 | 64.6 | black film |
| Ex. 1 | 16.7 (115.1) | 99.2 | 96.3 | dark brown soln, no film |
| Ex. 2 | 17.7 (122.0) | 101.4 | 99.0 | dark brown soln, no film |
| Ex. 3 | 18.7 (128.9) | 95.8 | 88.2 | dark brown soln, no film |

Comparative Experiment B shows substantial rhodium loss both by atomic absorption spectroscopy (AA) and visual appearance (rhodium black). Examples 1-3 show substantial improvement. While the analytical results show little to no loss, the visual appearance shows the beginnings of catalyst degradation but at a much reduced rate compared to the comparative experiment.

Examples 4-8 and C.E. D

Following the General Procedure, solutions of 300 ppm rhodium and 10 equivalents of ligand A in tetraglyme are charged to individual reactors. Following the 30-60 minute contact with 1:1 $CO:H_2$ gas, Comparative Experiment D (C.E. D) is flushed with nitrogen for about 60 minutes, then sealed at 165 psia (1138 kPa). The remaining reactors are flushed with CO for about 60 minutes and then sealed under the pressures shown in Table 2. After 6 days, the reactors are sampled to determine rhodium loss, and the results are summarized in Table 2.

TABLE 2

Examining the effect of CO at various pressures;
rhodium accountability at 110° C.

|  | CO psia (kPa) | % Original Rhodium by AA after 6 days |
|---|---|---|
| C. E. D | 0 | 20 |
| Ex. 4 | 19.7 (135.8) | 88 |
| Ex. 5 | 24.7 (170.3) | 86 |
| Ex. 6 | 29.7 (204.8) | 82 |
| Ex. 7 | 34.7 (239.2) | 105 |
| Ex. 8 | 39.7 (273.7) | 93 |

The results in Tables 1 and 2 show that rhodium loss is significantly reduced by maintaining an atmosphere of CO, and more specifically that pressures greater than 16 psia (110 kPa) provide the desired result.

Examples 9-11 and C.E. E

Following the General Procedure, solutions of 300 ppm rhodium and 10 equivalents of ligand A in tetraglyme are charged to individual reactors at 110° C. Following the 30-60 minute contact with 1:1 $CO:H_2$ gas, Comparative Example E (C.E. E) is flushed with nitrogen for about 60 minutes then sealed at 165 psia (1138 kPa). Ex 9 is flushed with CO for about 60 minutes, and then sealed under the pressure indicated in Table 3. The remaining reactors are flushed with mixtures of CO and $H_2$ for about 60 minutes, and then sealed under the atmospheres shown in Table 3. The reactors are sampled to determine rhodium loss, and the results are summarized in Table 3.

The results in Table 3 show that:
1) Catastrophic catalyst decomposition is observed in the absence of CO.
2) An atmosphere of 1:1 syngas provides some benefit relative to a CO-depleted environment. However, a CO-rich or nearly pure CO atmosphere is preferred.
3) An atmosphere of 1:1 syngas is beneficial relative to a 1:2 $CO:H_2$ atmosphere.
4) CO in the absence of $H_2$ provides the best performance.

Because hydroformylation with the rhodium catalysts may demonstrate a high order response to $[H_2]$, running under a hydrogen-rich atmosphere would be clearly beneficial for maximizing olefin conversion; however, this is not the best environment for the catalyst. The fact that maintaining an atmosphere enriched in carbon monoxide slows rhodium clustering highlights the ability to stabilize the catalyst in a strip-gas vaporizer (i.e., a vaporizer where flowing gas is utilized to enhance product removal).

Example 12-14 and C.E. F, G and H

The testing is conducted in 100 mL stirred stainless steel autoclaves equipped with mass flow meters for accurate control of carbon monoxide, hydrogen, and nitrogen, as well as electric heaters for accurate control of reactor temperatures. Each autoclave is charged with solutions of 185 ppm rhodium and 10 equivalents of Ligand A in 50 mL of toluene and flushed three times with 115 psia of 1:1 syn gas. The reactors are then pressurized to 115 psia with 1:1 syn gas and heated with stirring to 85° C. for 30 minutes, after which the heat is turned off, and the solutions are allowed to cool to room temperature. The reactors are vented and pressurized to 599.5-607.5 psia (4133.4-4188.6 kPa) with varying gas mixtures as indicated in Table 4. The solutions are heated to 110° C. with stirring for 4 days, after which the reactors are cooled and vented; the vent streams are analyzed by GC to confirm the gas compositions. The reactors are then disassembled; the rhodium concentration of each solution is measured by ICP and the appearance of each solution is noted. The results are summarized in Table 4.

TABLE 3

Examining the effect of CO and $H_2$ partial pressures;
rhodium accountability after heating at 110° C.

| | CO psia (kPa) | $H_2$ psia (kPa) | % of original rhodium by AA after | | | final solution appearance |
|---|---|---|---|---|---|---|
| | | | 1 day | 5 days | 8 days | |
| C.E. E | 0 | 0 | 47 | 30 | 30 | cloudy dark brown |
| Ex. 9 | 39.7 (273.7) | 0 | 102 | 93 | 88 | clear pale orange |
| Ex. 10 | 32.4 (223.4) | 32.4 (223.4) | 100 | 81 | 72 | clear orange-brown |
| Ex. 11 | 29.9 (206.2) | 59.8 (412.3) | 96 | 74 | 65 | clear brown |

Note:
the "0 psia" CO reactor is heated under nitrogen.

TABLE 4

Examining the effect of $H_2$ partial pressures on rhodium accountability at 110° C.

| | total pressure psia (kPa) | CO psia (kPa) | $H_2$ psia (kPa) | $N_2$ psia (kPa) | % original rhodium by ICP after 4 days | Final solution appearance |
|---|---|---|---|---|---|---|
| Ex. 12 | 599.5 (4133.4) | 599.4 (4132.7) | 0.06 (0.4) | 0 | 100 | clear yellow |
| Ex. 13 | 603.5 (4161.0) | 584.2 (4027.9) | 19.3 (133.1) | 0 | 96 | clear yellow |
| Ex. 14 | 607.5 (4188.6) | 586.2 (4041.7) | 21.3 (146.9) | 0 | 97 | clear yellow |
| C.E. F | 599.5 (4133.4) | 0 | 0.3 (2.1) | 599.2 (4131.3) | 82 | clear yellow |
| C.E. G | 603.5 (4161.0) | 0 | 18.1 (124.8) | 585.4 (4036.2) | 4 | clear orange, black precipitate |
| C.E. H | 607.5 (4188.6) | 0 | 21.9 (151.0) | 585.6 (4037.6) | 2 | colorless, black solids |

The results of Table 4 further establish the benefit of carbon monoxide and the deleterious effect of hydrogen.

Example 15

FIG. 1 illustrates a hydroformylation process with subsequent separation of aldehyde product and catalyst from the hydroformylation product stream, with recycle of a liquid catalyst stream back to the hydroformylation reaction zone and with a CO-containing stream being added to the stripping gas (line 55). The vaporizer process of FIG. 1 is modeled using ASPEN Plus software available from ASPEN Technology, Inc. of Cambridge, Mass., USA. No knock-out vessel between the reaction zone and the vaporizer is employed. The vent overhead from the vaporizer condenser is transferred back to the vaporizer via a blower 400 via line 24 and additional CO (95% purity) is added via line 55. The model assumes hydroformylation of a $C_8$ olefin with carbon monoxide and hydrogen in the presence of a rhodium-organophosphite ligand complex catalyst of Ligand A. As shown in Table 4, the ASPEN model provides mass balances for the FIG. 1 streams that are related to operation of the vaporizer. At steady state, the vaporizer 200 conditions are as follows: total pressure is 27.6 psia (190 kPa), CO partial pressure is 24.9 psia (172 kPa), and the vaporization zone temperature is 115° C. The vaporizer condenser 300 outlet process temperature is 40° C. The strip gas stream 20, the sum of streams 24 and 55, is at 31.9 psia (220 kPa) and 58° C. with 28.9 psia (199 kPa) CO partial pressure.

without any impact on the upstream hydroformylation reaction, i.e., a negligible amount of CO is transferred from the vaporizer to the reactor via stream 23. In the absence of stream 55, the vaporizer CO partial pressure would be less than 5 psia (34 kPa), as taught in U.S. Pat. No. 8,404,903. Table 4 also shows the removal of dimers and trimers, to model heavies, at their rate of formation, keeping their concentration in the reaction zone constant over time. Similar results can be obtained with other olefins as well, differing primarily in vaporizer total pressure and vaporizer temperature.

Example 16, 17 and Comparative Experiments I and J

The testing is conducted in a liquid recycle hydroformylation system that consists of three 1-liter stainless steel stirred tank reactors connected in series. The system is equipped with mass flow meters for accurate control of carbon monoxide, hydrogen, and nitrogen, as well as electric heaters for accurate control of reactor temperatures. A C8 olefin mixture is fed to the first reactor at a controlled rate. A portion of the liquid reaction solution is continuously fed from the final reactor to a flash vessel where initial separation of the gas and liquid take place. The flash vessel is purged with nitrogen and the liquid effluent is filtered and fed to a distributor plate on top of a heated, vertically mounted tube (vaporizer). The liquid effluent flows down the surface of the tube within the vaporizer under a stream of

TABLE 5

Mass flows for input/output of vaporizer with added CO to stripping gas.

| Stream ID | 21 | 22 | 23 | 24 | 25 | 26 | 55 |
|---|---|---|---|---|---|---|---|
| Flow (kg/hr) | 25300 | 90312 | 12550 | 77562 | 223 | 12527 | 200 |
| Mass Flow (kg/hr) | | | | | | | |
| Inerts | <0.1 | 3468 | <0.1 | 3458 | 10 | <0.1 | 10 |
| $H_2$ | .8 | 265 | <0.1 | 264 | 1 | <0.1 | 0 |
| CO | 17 | 72152 | .03 | 71952 | 207 | <0.1 | 190 |
| Octenes/Octanes | 1255 | 2736 | 97.5 | 1578 | 4.6 | 1153 | 0 |
| Nonals | 17602 | 11668 | 6244 | 310 | 1 | 11357 | 0 |
| Dimers and Trimers | 6224 | 16 | 6208 | <0.1 | <0.1 | 16 | 0 |

Table 5 shows that with a very small stream 55, compared to the total production rate 26, added as CO stream, the CO partial pressure is readily controlled at >24 psia (165 kPa)

flowing gas (strip gas). The flow rate of the strip gas is controlled using a control valve upstream of a compressor and the flow is accurately measured using a flow meter downstream of the compressor; the mole percent composition of the strip gas is determined by GC analyses. The effluent stream from the vaporizer is sent to a gas-liquid separator located at the bottom of the vaporizer, where vaporized aldehyde is separated from the non-volatile components of the liquid reaction solution. The vaporized aldehyde product is condensed and collected in a product receiver; the non-volatile components, comprising residual aldehyde, aldehyde heavies and concentrated catalyst, are pumped back to the first reactor in the series. The volatile, non-condensable gases are recycled using a compressor and utilized for the strip gas.

The continuous 3-liter hydroformylation system is initially charged with a solution of rhodium and Ligand A in mixed C8 olefin and toluene; during the course of continuous operation, the product aldehyde and aldehyde heavy condensation products begin to serve as the reaction solvent (e.g. after approximately two days). Reaction parameters are established as summarized in Table 6:

TABLE 6

Reaction parameters for continuous operation of the 3-liter reaction system

| | |
|---|---|
| Reactor 1 1:1 $CO:H_2$ | 290 psia (1999.5 kPa) |
| Reactor 2 1:1 $CO:H_2$ | 261 psia (1799.5 kPa) |
| Reactor 3 1:1 $CO:H_2$ | 232 psia (1599.6 kPa) |
| Reactor temp (all) | 85° C. |
| moles Ligand A: mole Rhodium | 8-12 |
| flash vessel pressure | 50.8 psia (350.3 kPa) |
| flash vessel temperature | 22° C. |
| vaporizer pressure | 21.8 psia (150.3 kPa) |
| vaporizer temp | 110° C. |
| Strip gas flow rate | 300-520 L/hr |
| C8 olefin feed rate | 107.5 g/hr |
| reactor residence time | 28 hr |
| production rate | 0.32 gmol/hr |

The strip gas composition is varied and the impact on rhodium loss is measured throughout the system using ICP. The results are summarized in Table 7.

TABLE 7

Impact of strip gas composition on rhodium loss

| | | Strip gas composition | | | |
|---|---|---|---|---|---|
| Segment | duration of test (days) | CO partial pressure psia (kPa) | $H_2$ partial pressure psia (kPa) | $N_2$ partial pressure psia (kPa) | Rhodium loss (ppm/day) |
| C.E. I | 1 | 10 | 10.9 (75.2) | 10.9 (75.2) | 0 | 0.9 |
| Ex. 16 | 2 | 17 | 21.72 (149.6) | 0.04 (0.28) | 0 | 0 |
| C.E. J | 3 | 33 | 0 | 0 | 21.76 (150.0) | 1.1 |
| Ex. 17 | 4 | 13 | 21.72 (149.6) | 0.04 (0.28) | 0 | 0 |

The results in Table 7 show that;

The highest rhodium loss occurs when the strip gas is predominantly nitrogen (C.E. J)

A strip gas comprised of syn gas (C.E. I) reduces the rate of rhodium loss relative to a nitrogen strip gas (C.E. J).

The best results are achieved when the strip gas is predominantly CO (Ex. 16 and 17).

The deleterious effect of hydrogen is once again demonstrated (C.E. I compared to Examples 16 and 17).

What is claimed is:

1. A continuous hydroformylation process comprising: (a) removing a reaction fluid from a reactor; (b) sending the reaction fluid to a vaporizer; (c) separating the reaction fluid in the vaporizer to produce a catalyst-containing liquid stream and a gas phase stream; and (d) maintaining an average CO partial pressure in the vaporizer of greater than 16 psia (110 kPa).

2. A continuous hydroformylation process comprising:
  (a) feeding a reaction fluid comprising one or more products, one or more heavy by-products, a transition metal-organophosphite ligand complex catalyst, one or more unconverted reactants, and one or more inert lights into a vaporizer;
  (b) removing from the vaporizer an overhead gas stream comprising one or more products, one or more unconverted reactants, one or more inert lights, and a portion of the heavy by-products, and feeding said overhead gas stream into a condenser;
  (c) removing from the condenser a condenser overhead gas stream comprising one or more unconverted reactants and one or more inert lights;
  (d) recycling at least a portion of said condenser overhead gas stream to the vaporizer;
  (e) introducing to the vaporizer, in addition to the condenser overhead gas stream, a gas stream comprising CO, such that the average CO partial pressure in the vaporizer is greater than 16 psia (110 kPa); and
  (f) removing as a tails stream from the vaporizer, a liquid recycle catalyst stream comprising the transition metal-organophosphite ligand complex catalyst and the balance of the heavy by-products.

3. The process of claim 1 wherein the average CO partial pressure in the vaporizer is at least 20 psia (138 kPa).

4. The process of claim 1 wherein the average CO partial pressure in the vaporizer is at least 25 psia (172 kPa).

5. The process of claim 1 wherein the process outlet temperature of the vaporizer is at least 80° C.

6. The process of claim 1 wherein the product comprises an aldehyde.

7. The process of claim 1 wherein, in the vaporizer, the $H_2$ partial pressure is from 0.1 psia (0.7 kPa) to less than half the CO partial pressure.

8. The process of claim 1 wherein, in the vaporizer, the $H_2$ partial pressure is from 0.1 psia (0.7 kPa) to no more than 10% of the CO partial pressure.

9. The process of claim 1 wherein the reaction fluid is obtained by contacting CO, $H_2$, an olefin and a catalyst comprising rhodium and an organophosphite ligand in a reaction zone under hydroformylation reaction conditions to produce an aldehyde product in the reaction fluid.

10. The process of claim 1 wherein the catalyst is a transition metal-organophosphite ligand complex catalyst, wherein the ligand comprises an organomonophosphite ligand.

11. The process of claim 1, further comprising maintaining an average $H_2$ partial pressure in the vaporizer of less than 2 psia (14 kPa).

12. The process of claim 1, further comprising sending the reaction fluid to a flash vessel prior to sending the reaction fluid to the vaporizer.

* * * * *